United States Patent
Siddalingappa

(10) Patent No.: US 11,730,815 B2
(45) Date of Patent: *Aug. 22, 2023

(54) STABLE LIQUID PHARMACEUTICAL COMPOSITIONS COMPRISING BENDAMUSTINE

(71) Applicant: GOOD HEALTH, LLC, Princeton, NJ (US)

(72) Inventor: Basavaraj Siddalingappa, Gujarat (IN)

(73) Assignee: GOOD HEALTH, LLC, Princeton, NJ (US)

( * ) Notice: Subject to any disclaimer, the term of this patent is extended or adjusted under 35 U.S.C. 154(b) by 20 days.

This patent is subject to a terminal disclaimer.

(21) Appl. No.: 16/879,207

(22) Filed: May 20, 2020

(65) Prior Publication Data

US 2020/0297849 A1    Sep. 24, 2020

Related U.S. Application Data

(63) Continuation-in-part of application No. 16/806,120, filed on Mar. 2, 2020, which is a continuation-in-part of application No. 16/695,428, filed on Nov. 26, 2019, now abandoned.

(60) Provisional application No. 62/771,271, filed on Nov. 26, 2018.

(51) Int. Cl.
*A61K 47/10*     (2017.01)
*A61K 47/22*     (2006.01)
*A61K 47/40*     (2006.01)
*A61K 31/4184*   (2006.01)

(52) U.S. Cl.
CPC .......... *A61K 47/10* (2013.01); *A61K 31/4184* (2013.01); *A61K 47/22* (2013.01); *A61K 47/40* (2013.01)

(58) Field of Classification Search
CPC .... A61K 31/4184; A61K 47/10; A61K 47/40; A61K 47/22
See application file for complete search history.

(56) References Cited

U.S. PATENT DOCUMENTS

| | | | |
|---|---|---|---|
| 8,344,006 B2 | 1/2013 | Drager et al. | |
| 8,436,190 B2 | 5/2013 | Brittain et al. | |
| 8,609,707 B2 | 12/2013 | Palepu et al. | |
| 8,703,964 B2 * | 4/2014 | Popek | A61K 9/19 548/304.4 |
| 8,791,270 B2 | 7/2014 | Brittain et al. | |
| 9,000,021 B2 * | 4/2015 | Sundaram | A61P 35/00 514/396 |
| 9,034,908 B2 | 5/2015 | Sundaram | |
| 9,144,568 B1 | 9/2015 | Sundaram | |
| 9,265,831 B2 | 2/2016 | Palepu et al. | |
| 9,572,796 B2 | 2/2017 | Palepu et al. | |
| 9,572,797 B2 | 2/2017 | Palepu et al. | |
| 9,572,887 B2 | 2/2017 | Sundaram | |
| 9,572,888 B2 | 2/2017 | Sundaram | |
| 9,579,384 B2 | 2/2017 | Sundaram et al. | |
| 9,597,397 B2 | 3/2017 | Sundaram | |
| 9,597,398 B2 | 3/2017 | Sundaram | |
| 9,597,399 B2 | 3/2017 | Sundaram | |
| 9,603,930 B2 | 3/2017 | Patel | |
| 10,010,533 B2 | 7/2018 | Palepu et al. | |
| 10,052,385 B2 | 8/2018 | Sundaram | |
| 2006/0159713 A1 | 7/2006 | Brittain et al. | |
| 2011/0184036 A1 | 7/2011 | Palepu et al. | |
| 2013/0210878 A1 | 8/2013 | Soppimath et al. | |
| 2013/0210879 A1 | 8/2013 | Palepu et al. | |
| 2014/0213650 A1 | 7/2014 | Pipkin et al. | |
| 2016/0158362 A1 | 6/2016 | Patel | |
| 2018/0000789 A1 | 1/2018 | Palepu et al. | |
| 2018/0055823 A1 | 3/2018 | Patel | |
| 2018/0296535 A1 | 10/2018 | Palepu et al. | |
| 2018/0296536 A1 | 10/2018 | Palepu et al. | |
| 2019/0350904 A1 | 11/2019 | Palepu et al. | |

FOREIGN PATENT DOCUMENTS

| | | | |
|---|---|---|---|
| DE | 159289 A1 | 3/1983 | |
| WO | 2011/103150 A2 | 8/2011 | |
| WO | 2015/104720 A2 | 7/2015 | |
| WO | 2016/005995 A2 | 1/2016 | |
| WO | WO-2016005995 A2 * | 1/2016 | ........... A61K 9/0019 |
| WO | 2017/175098 A1 | 10/2017 | |
| WO | 2018/045136 A1 | 3/2018 | |
| WO | 2020/035806 A1 | 2/2020 | |

OTHER PUBLICATIONS

U.S. Appl. No. 62/723,725, filed Aug. 28, 2018.
U.S. Appl. No. 62/764,975, filed Aug. 17, 2018.
U.S. Appl. No. 62/815,376, filed Mar. 8, 2019.
Mottu et al., "Organic Solvents for Pharmaceutical Parenterals and Embolic Liquids: A Review of Toxicity Data," PDA J Pharm Sci and Tech 54:456-469 (2000).
Prasanna et al., "Preparation and Evaluation of Bendamustine Hydrochloride Aqueous Formulations," Int. J. Pharm. Res. Scholars 2(2):110-113 (2013).
Prasanna et al., "Preparation and Evaluation of Bendamustine Hydrochloride Non Aqueous Formulations," Int. J. Pharm. Res. Scholars 2(2):136-139 (2013).
Treanda® Prescribing Information, Revised Oct. 2008.
Belrapzo® Prescribing Information, Revised Aug. 2018.
Bendeka® Prescribing Information, Revised Dec. 2015.
U.S. Appl. No. 61/208,541, filed Feb. 25, 2009.
U.S. Appl. No. 61/269,944, filed Jul. 1, 2009.
Prasanna et al., "Preparation and Evaluation of Bendamustine Hydrochloride Aqueous Formulations," International Journal for Pharmaceutical Research Scholars (IJPRS) 2:110-113 (2013).
Gidwani et al., "Inclusion complexes of bendamustine with β-CD, HP-β-CD and Epi-β-CD: In-vitro and in-vivo evaluation," Drug Dev. Ind. Pharm. 41(12):1978-1988 (2015).

(Continued)

*Primary Examiner* — Timothy P Thomas
(74) *Attorney, Agent, or Firm* — Raphael Bellum PLLC

(57) ABSTRACT

The invention is directed to stable liquid pharmaceutical compositions comprising, consisting of, or consisting essentially of bendamustine, at least one cyclodextrin, at least one non-aqueous solvent, at least about 2% water v/v of the composition, and at least one antioxidant, and their use for treating cancers, their preparation, and dosage forms containing them.

19 Claims, No Drawings

(56) References Cited

OTHER PUBLICATIONS

Loftsson et al., "Pharmacokinetics of cyclodextrins and drugs after oral and parenteral administration of drug/cyclodextrin complexes," J. Pharm. Pharmacol. 68:544-555 (2016).
Jambhekar et al., "Cyclodextrins in pharmaceutical formulations II: solubilization, binding constant, and complexation efficiency," Drug Discov. Today 21(2):363-368 (2016).

* cited by examiner

STABLE LIQUID PHARMACEUTICAL COMPOSITIONS COMPRISING BENDAMUSTINE

CROSS-REFERENCE TO RELATED APPLICATIONS

This application is a continuation-in-part application of U.S. patent application Ser. No. 16/806,120, filed Mar. 2, 2020, which is a continuation-in-part application of U.S. patent application Ser. No. 16/695,428, filed Nov. 26, 2019, which claims benefit of U.S. Provisional Application No. 62/771,271, filed Nov. 26, 2018, the disclosure of each of which is incorporated herein by reference.

FIELD OF THE INVENTION

This invention relates to stable liquid pharmaceutical compositions of bendamustine, and methods for their use and preparation.

BACKGROUND OF THE INVENTION

Parenteral administration of drugs requires adequate solubility and stability in aqueous fluid. Hence, some drugs are formulated as dry powder parenteral (lyophilized powders) to avoid precipitation and degradation during storage. Such products are intended to be reconstituted just before injection, but such reconstituted solutions will have limited stability.

Bendamustine (4-(5-(bis(2-chloroethyl)amino)-1-methyl-1H-benzo[d]imidazol-2-yl)butanoic acid), for example, is an anticancer agent used in the treatment of many cancers, including chronic lymphocytic leukemia (CLL), multiple myeloma, and indolent B-cell non-Hodgkin's lymphoma (NHL). Treanda® (bendamustine HCl) injection was initially formulated as a lyophilized powder, which requires a long time, about 15-30 minutes, for reconstitution. Furthermore, the labeling instructions of Treanda® suggests that reconstituted solutions need to be diluted further with isotonic diluents up to 500 mL within 30 minutes. Moreover, such solutions need to be used within three hours, and, if needed, should be stored at 2-8° C. for not more than 24 hours.

The main pathway for degradation of bendamustine in aqueous solution is hydrolysis. Instead of addition elimination type of hydrolysis, bendamustine undergoes direct substitution with the reactive chlorine groups in its structure. See Scheme 1. The two main hydrolysis products have RRTs (relative retention times) of 0.6 and 0.2, respectively.

Scheme 1: Chemical Structure of Bendamustine

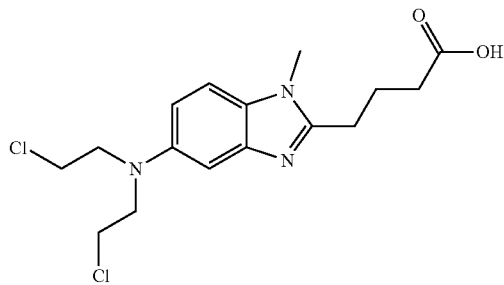

In the view of the stability and reconstitution issues associated with the lyophilized formulation of bendamustine, recently, several products have been introduced to the market which are ready-to-use solutions of bendamustine after appropriate dilution with isotonic solutions.

Treanda® ready-to-use solution bendamustine HCl formulation comprises 66% N,N-dimethylacetamide (DMA) and 34% propylene glycol (PG). The product is reported to be stable for 24 hours when stored under refrigerated conditions at 2-8° C., or for only two hours when stored at room temperature conditions of 15-30° C. However, DMA is incompatible with closed system transfer devices (CSTD), adapters, and syringes containing polycarbonate or acrylonitrile-butadiene-styrene (ABS). Most commonly used transfer devices/infusion accessories are made of ABS or polycarbonate. Therefore, the Treanda® ready-to-use solution has FDA restrictions regarding its use with such devices.

Similarly, another ready-to-use bendamustine HCl formulation, Bendeka®, has been in the market for some time. The formulation comprises polyethylene glycol (PEG) 400 and PG (90:10), and is reported to be stable when stored refrigerated (2-8° C.) or for only three hours when stored at room temperature (15-30° C.).

The common practice to formulate injectable solutions of drugs is to include non-aqueous, organic solvents in the compositions to improve solubility. Sometimes, the pure mixture of non-aqueous solvents achieves the desired solubility and stability. Recognizing the inherent difficulties in formulating ready-to-use bendamustine solutions, various approaches have been disclosed.

For example, DE 159289 discloses a ready-to-use injectable solution of bendamustine HCl that avoids lyophilization. DE 159289 describes an anhydrous solution of bendamustine hydrochloride in PG or ethanol. As per TLC analysis, no new impurities were present in the product made using 100% PG.

U.S. Pat. No. 8,344,006 discloses liquid ready-to-use compositions of bendamustine comprising 34% PG and 66% DMA. The product is reported to be stable for at least 2 years when stored in a refrigerator at 2-8° C. However, the formulations are not stable in 25° C./60% relative humidity (RH) for more than six months. U.S. Pat. No. 8,344,006 also discloses that formulation in 100% PG was not feasible due to instability.

U.S. Pat. No. 8,609,707 discloses liquid compositions of bendamustine which are stable with total impurities less than 5% based on peak area response. The compositions consist of a mixture of PEG and PG in a 90:10 ratio. The compositions also include an antioxidant. However, these compositions must be stored in the refrigerator at 2-8° C.

US 2013/0210879 discloses bendamustine liquid compositions comprising PEG/PG, and an additional pH adjusting agent to maintain pH of the composition between 6-11. Adjusting the pH closer to a neutral pH demonstrated improved stability with respect to the unwanted formation of PG/PEG esters of bendamustine.

U.S. Pat. No. 9,265,831 discloses non-aqueous liquid bendamustine compositions comprising bendamustine, a fluid comprising 5-10% v/v of PG, PEG, and an antioxidant, with a PEG:PG ratio or between 90:5 to 75:25.

U.S. Pat. No. 9,144,568 discloses diluted liquid compositions of 0.5-5.6 mg/mL bendamustine, a solubilizer comprising PEG and PG with concentrations of 0.5-26.5%, a parenterally acceptable diluent, and an optional antioxidant.

U.S. Pat. No. 9,034,908 also describes a dilute bendamustine composition comprising 0.05 to 12.5 mg/mL of bendamustine, a solubilizer comprising PEG and PG, where the PEG and PG are present at a concentration of 0.3-45% and 0.03-5% v/v, respectively, a parenterally acceptable diluent, and an optional antioxidant. This composition, however, must be administered within 10 minutes.

U.S. Pat. No. 9,000,021 discloses parenterally administering to a patient a volume of 100 ml or less of a fluid composition containing 0.05 to 12.5 mg/mL of bendamustine, a solubilizer comprising PEG and PG, where the PEG and PG are present at a concentration of 0.3 to 45% and 0.03 to 5% v/v, respectively, and an optional parenterally acceptable diluent. This composition, however, must be administered within 30 minutes.

WO 2016/005995 discloses compositions for bendamustine prepared using organic solvents, other than glycols, and disaccharide syrup, particularly sucrose syrup in water. The compositions also contain cysteine and antioxidants. The compositions are semi-aqueous with at least 5-10% of water.

US 2014/0213650 discloses dry powder formulations of nitrogen mustard compounds, preferably Melphalan. The composition includes a cyclodextrin derivative and Melphalan in a single vial. However, the powder mixtures are prepared by either lyophilization or spray drying.

US 2016/0158362 discloses compositions of bendamustine in a solvent mixture comprising DMA and glycerin.

U.S. Pat. No. 9,572,887 highlights the usefulness of compositions when the dilute infusion solution needs to be more concentrated and holding of drug in solution while dilute solutions are refrigerated.

U.S. Pat. No. 8,703,964 discloses compositions of bendamustine in an aqueous solution containing ionic cyclodextrins. However, the stability of such solutions is not adequate, as their $T_{1/2}$ (degradation) is about 780 minutes. Hence, these liquid compositions are not stable for extended periods.

Prasanna et al., "Preparation and Evaluation of Bendamustine Hydrochloride Aqueous Formulations," Int. J. Pharm. Res. Scholars 2(2):110-113 (2013), reported that bendamustine compositions with cyclodextrin derivatives in aqueous solutions are unstable.

Prasanna et al., "Preparation and Evaluation of Bendamustine Hydrochloride Non Aqueous Formulations," Int. J. Pharm. Res. Scholars 2(2):136-139 (2013), reported non-aqueous formulations of bendamustine in solvents consisting of DMA, ethanol, PEG, and mixtures of those solvents.

WO 2011/103150 discloses lyophilized preparations of bendamustine with various cyclodextrins. However, no liquid compositions are described.

None of the above examples describe ready-to-use, liquid bendamustine compositions, which are stable for extended periods of time at room temperature, either with or without cyclodextrin, and which have no or substantially no impurities. Also, there is no disclosure of enhancing solubility and stability of bendamustine in non-aqueous solvents by cyclodextrins. And to our knowledge, there are no reports about cyclodextrin improving the solubility of bendamustine in solvents where cyclodextrin itself is insoluble.

And to our knowledge, the prior art also does not describe improved solubility and stability of bendamustine in semi-aqueous formulations, nor does it describe the non-effectiveness of cyclodextrins in stabilizing bendamustine in systems containing predominantly an aqueous component.

While cyclodextrins are known to improve the solubility and stability of drugs, compositions containing cyclodextrins are either solids, aqueous solutions, or semi-aqueous solutions, based on the need and chemical nature of the molecule being formulated. A greater stabilization effect of cyclodextrin is seen if the drug has a greater affinity for the cyclodextrin cavity. If the drug and cyclodextrin are present in a solvent system, where both are freely soluble, there will be no or very minimal interaction between two. Hence, drug tends to be outside the cavity. However, if the solvent system is unfavorable for the drug, it will be suspended in such a solvent. If cyclodextrin is added, because of unfavorable conditions, the drug interacts with cyclodextrin and gets encapsulated in its cavity. Because of the inclusion in the cavity, a drug gets protection against solvent mediated degradation.

Cyclodextrin-containing compositions of bendamustine made with a combination of a non-aqueous solvent and water are not described. This invention describes such compositions for improving the solubility and stability of bendamustine.

SUMMARY OF THE INVENTION

The invention relates to stable liquid pharmaceutical compositions comprising, consisting of, or consisting essentially of bendamustine, at least one cyclodextrin, at least one non-aqueous solvent, at least about 2% water v/v of the composition, and at least one antioxidant.

The invention further relates to methods of treating cancer comprising the administration of an effective amount of the stable liquid pharmaceutical compositions of the invention to a mammal (e.g., a human) in need thereof.

The invention also relates to methods of making the stable liquid pharmaceutical compositions of the invention.

The invention further relates to dosage forms containing the stable liquid pharmaceutical compositions of the invention.

DETAILED DESCRIPTION OF THE INVENTION

The invention relates to stable liquid pharmaceutical compositions comprising, consisting of, or consisting essentially of bendamustine or a pharmaceutically acceptable salt, ester, or prodrug thereof, at least one cyclodextrin, at least one non-aqueous solvent, at least about 2% water v/v of the composition, and at least one antioxidant.

Preferably, the stable liquid pharmaceutical compositions of the invention comprise, consist of, or consist essentially of bendamustine or a pharmaceutically acceptable salt, ester, or prodrug thereof, at least one cyclodextrin, at least one non-aqueous solvent, at least about 2 to about 60% water v/v of the composition (e.g., about 2.5 to about 55%, about 3 to about 55%, about 5 to about 50%, about 10 to about 45%, about 15 to about 40%, about 20 to about 35%, about 25 to about 30% water v/v of the composition), and at least one antioxidant. The at least one non-aqueous solvent comprises the remaining volume of the composition, such that the composition comprises about 40 to about 98% v/v non-aqueous solvent when the water comprises from about 2 to about 60% v/v of the composition; about 45 to about 97.5% v/v non-aqueous solvent when the water comprises from about 2.5 to about 55% v/v of the composition; about 45 to about 97% v/v non-aqueous solvent when the water comprises from about 3 to about 55% v/v of the composition; about 50 to about 95% v/v non-aqueous solvent when the water comprises from about 5 to about 50% v/v of the composition; about 55 to about 90% v/v non-aqueous solvent when the water comprises from about 10 to about 45% v/v of the composition; about 60 to about 85% v/v non-aqueous solvent when the water comprises from about 15 to about 40% v/v of the composition; about 65 to about 80% v/v non-aqueous solvent when the water comprises from about 20 to about 35% v/v of the composition; and about 70 to about 75% v/v non-aqueous solvent when the water comprises from about 25 to about 30% v/v of the composition. The compositions may also contain at least about 30 to about 60% water v/v of the composition (e.g., about 35 to about 60%, about 40 to about 55%, about 45 to about 50%) and the balance being the at least one non-aqueous solvent (e.g., about 70 to about 40%, about 65 to about 40%, about 60 to about 45%, about 55 to about 50% v/v of the composition).

The term "v/v" means "volume per volume" and is used herein to express the concentration of a substance in a solution on a volume per volume basis. By way of example, a solution containing 50% v/v non-aqueous solvents means that there are about 50 ml of combined non-aqueous solvents in every 100 ml of said solution. As another example, one liter of a composition of the invention containing 2.5% v/v water contains 25 ml water, and one liter of a composition of the invention containing 3% water contains 30 ml water.

Surprisingly, it was found that stable compositions of bendamustine can be prepared using a combination of at least one non-aqueous solvent, at least about 2% water v/v of the composition, at least one cyclodextrin, and at least one antioxidant. As used herein, a "stable" composition of the invention means a pharmaceutical composition which contains ≤6% total impurities in the composition resulting from the degradation of bendamustine in the composition, as measured by HPLC at a wavelength of 220 nm after ≥18 months at about 25° C./60% relative humidity (RH), and ≤5% total impurities in the composition resulting from the degradation of bendamustine in the composition, as measured by HPLC at a wavelength of 220 nm after ≥2 years at about 2-8° C. For example, the compositions of the invention have sufficient stability at room temperature and refrigerated conditions to have utility as a pharmaceutical product even after storage for extended periods.

Advantageously, the compositions of the invention have sufficient stability to allow for storage at room temperature conditions (about 25° C./60% RH) for ≥1 month (e.g., ≥6 months, ≥1 year, ≥18 months, ≥2 years), with ≥90% of un-degraded bendamustine (e.g., ≥91%, ≥92%, ≥93%, ≥94%, ≥95%, ≥96%, ≥97%, ≥98%, ≥99%) and with total impurities ≤6% (e.g., ≤5%, ≤4%, ≤3%, ≤2%, ≤1%, ≤0.1%), as determined by HPLC at a wavelength of 220 nm. For example, the compositions of the invention may contain total impurities ≤3% in the composition resulting from the degradation of bendamustine in the composition, as determined by HPLC at a wavelength of 220 nm, at about 25° C./60% relative humidity for ≥6 months; the compositions of the invention may contain total impurities ≤5% in the composition resulting from the degradation of bendamustine in the composition, as determined by HPLC at a wavelength of 220 nm, at about 25° C./60% relative humidity for ≥1 year; and the compositions of the invention may contain total impurities ≤6% in the composition resulting from the degradation of bendamustine in the composition, as determined by HPLC at a wavelength of 220 nm, at about 25° C./60% relative humidity for ≥18 months.

Another advantage of the compositions of the invention is that they have sufficient stability to allow for storage at refrigerated conditions (about 2-8° C.) for ≥1 year (e.g., ≥2 years, ≥3 years, ≥4 years), with ≥90% of un-degraded bendamustine (e.g., ≥91%, ≥92%, ≥93%, ≥94%, ≥95%, ≥96%, ≥97%, ≥98%, ≥99%) and with total impurities ≤6% (e.g., ≤5%, ≤4%, ≤3%, ≤2%, ≤1%, ≤0.1%), as determined by HPLC at a wavelength of 220 nm. For example, the compositions of the invention may contain total impurities ≤5% in the composition resulting from the degradation of bendamustine in the composition, as determined by HPLC at a wavelength of 220 nm, at about 2-8° C. for ≥2 years.

The "stable" compositions of the invention may have a potency of ≥80% (e.g., ≥85%, ≥90%, ≥98%) of the bendamustine when stored at room temperature or refrigerated conditions.

The term "bendamustine" includes the chemical compound bendamustine or a pharmaceutically acceptable salt, ester, or prodrug thereof. In compositions of the invention, bendamustine may be present as itself or as a pharmaceutically acceptable salt, ester, or prodrug thereof. Preferably, the bendamustine is in the form of its hydrochloride salt. The amount of bendamustine present in the compositions of the invention may vary depending on the amount necessary for therapeutic administration. For example, the bendamustine may be present in the compositions of the invention in any amount, such as an amount ranging from about 0.01 to about 100 mg/mL, preferably about 0.1 to about 50 mg/mL, more preferably about 2 to about 30 mg/mL, even more preferably about 5 to about 25 mg/mL, and more preferably about 10 to about 25 mg/mL. The compositions of the invention may contain about 0.1 to about 50 wt %, preferably about 1 to about 30 wt %, more preferably about 1 to about 20 wt %, even more preferably about 1 to about 20 wt %, and even more preferably about 1 to about 10 wt %, of the bendamustine. These dosage ranges are not intended to be limiting. A practitioner skilled in the art may likewise administer suitable compositions of the invention in single or divided doses, according to the desired therapeutic effect. Thus, in certain clinical situations it may be desirable to administer compositions of the invention to give initial high levels of the bendamustine, followed by lower dose maintenance doses.

The compositions of the invention also contain at least one cyclodextrin. Particularly preferred cyclodextrins are hydroxypropyl-β-cyclodextrin, hydroxypropyl-γ-cyclodextrin, sulfobutyl ether β-cyclodextrin, or mixtures thereof. Most preferably, the cyclodextrin is hydroxypropyl-β-cyclodextrin.

The at least one cyclodextrin may be present in the compositions of the invention in any amount effective to stabilize the bendamustine. The cyclodextrin is typically present in an amount from 0.1 to about 40 wt % of the liquid composition. Preferably, the cyclodextrin is present in an amount ranging from about 20 to about 30 wt % of the liquid composition. The cyclodextrin may also be present in an amount ranging from about 10 to about 20 wt % of the liquid composition. More preferably, the cyclodextrin is present in an amount ranging from about 0.5 to about 10 wt % of the liquid composition. Most preferably, the cyclodextrin is present in an amount of about 0.25 wt %, about 2.5 wt %, or about 5 wt % of the liquid composition.

The composition of the invention also includes at least one non-aqueous solvent. The term "non-aqueous solvent" means a solvent that contains minimal or no water. The term "minimal" in the context of the non-aqueous solvent means a solvent that contains less than 1.0% v/v, preferably less than 0.1% v/v, more preferably less than 0.01% v/v, even more preferably less than 0.001% v/v, water. The non-aqueous solvent may comprise at least one organic compound selected from polysorbates, polyethylene glycol (PEG) polymers, polyalkoxylated castor oils, N,N-dimethylacetamide, dimethyl sulfoxide, 1-methyl-2-pyrrolidinone, and organic small molecule alcohols. In further embodiments, the organic small molecule alcohols are selected from ethanol, isopropyl alcohol, benzyl alcohol, and propylene glycol (PG). Preferred non-aqueous solvents are PEGs having an average molecular weight ranging from 200 g/mol to 1000 g/mol (e.g., PEG 200, PEG 300, PEG 400, PEG 500, PEG 600, PEG 700, PEG 800, PEG 900, PEG 1000), in particular, PEG 400, PEG 600, and mixtures thereof.

Also preferred are compositions of the invention which contain less than 1 wt %, preferably less than 0.1 wt %, more preferably less than 0.01 wt %, even more preferably less than 0.001 wt %, most preferably no organic small molecule alcohols (e.g., ethanol, isopropyl alcohol, benzyl alcohol, and PG). For example, one preferred composition of the invention comprises, consists essentially of, or consists of at least one PEG having an average molecular weight ranging from 200 g/mol to 1000 g/mol (e.g., PEG 400, PEG 600, or mixtures thereof) as the non-aqueous solvent, but less than 1 wt %, preferably less than 0.1 wt %, more preferably less than 0.01 wt %, even more preferably less than 0.001 wt %, most preferably no organic small molecule alcohols (e.g., ethanol, isopropyl alcohol, benzyl alcohol, and PG). Another preferred composition of the invention contains at least one non-aqueous solvent selected only from PEGs having an average molecular weight ranging from 200 g/mol to 1000 g/mol, preferably PEG 400, PEG 600, or mixtures thereof.

Typically, the at least one non-aqueous solvent is one in which the bendamustine, independent of the at least one cyclodextrin, is moderately or slightly soluble in the solvent(s), and the at least one cyclodextrin, independent of the bendamustine, is not soluble or sparingly soluble in the solvent(s). In the context of the bendamustine, the phrases "moderately soluble" or "slightly soluble" mean that the bendamustine solubility ranges between about 1 to about 30 mg/mL in a given solvent. And in the context of the cyclodextrin, the phrase "sparingly soluble" means that the cyclodextrin solubility is not more than about 1 to about 10 mg/mL in a given solvent.

The composition of the invention also contains water. For example, the water may be present in the form of as water-for-injection or any other solutions with water as a major component, such as aqueous buffers (e.g., citrate, phosphate, acetate in water), solutions of tonicity adjusting agents in water (e.g., sodium chloride solution, dextrose, amino acids), and mixtures thereof.

The compositions of the invention also include at least one antioxidant. Preferably, the antioxidant is selected from the group consisting of monothioglycerol (MTG), tocopherols (e.g., α-tocopherol), butylated hydroxyl anisole, butylated hydroxyl toluene (BHT), inorganic sulfates (e.g., sodium sulfate and metabisulfate), aromatic compounds (e.g., gallic acid, gentistic acid, vannilic acid), and mixtures thereof. The antioxidants may be present in the compositions of the invention in an amount ranging from about 0.01 to about 10 wt %, preferably from about 0.02 to about 10 wt %, more preferably about 0.02 to about 1 wt %, and even more preferably about 0.04 to about 0.5 wt %.

The compositions of the invention may also include at least one pharmaceutically acceptable excipient, such as surfactants, antimicrobials, preservatives, alkalizers and pH modifying agents, and the like. Exemplary surfactants include, but are not limited to, poloxamers, tweens, spans, and other fatty acid esters. Exemplary antimicrobials include, but are not limited to, benzoic acid, methyl and propyl parabens. Exemplary preservatives include, but are not limited to, parabens, benzoates, alcohols, quaternary ammonium salts. Exemplary alkalizers and pH modifying agents include, but are not limited to, sodium hydroxide, potassium hydroxide, tromethamine, lysine, arginine, glycine, meglumine and other appropriate bases.

The compositions of invention may also include additional solubilizers, such as, for example, salt forming agents, complexing agents, polymeric micelle forming agents, and other appropriate excipients which aid solubilization of drugs.

The pharmaceutically acceptable excipient and/or solubilizers may be present in the compositions of the invention in amounts typically known and used in the pharmaceutical formulation art.

Methods of Treatment Using the Compositions of the Invention

The invention also relates to methods of treating cancers, which comprises administering an effective amount of the compositions of the invention to a mammal (e.g., human, equine, bovine, ovine, canine, feline, porcine) in need thereof. For example, bendamustine compositions of the invention may be used to treat cancers, such as chronic lymphocytic leukemia (CLL), multiple myeloma, and/or indolent B-cell non-Hodgkin's lymphoma. In addition, the invention features the use of a dosage form of the invention for the manufacturing of a medicament for the treatment of cancers.

The compositions of the invention can be administered to the mammal in need thereof parenterally, such as by subcutaneous, intramuscular, or intravenous routes. The compositions may be administered directly, without dilution, for example, by injection as short infusion. Alternatively, they may be diluted further with pharmaceutically acceptable diluents (e.g., solutions of dextrose, sodium chloride, sodium lactate, an amino acid, glycerol, sorbitol, dextrose, mannitol, and mixtures thereof) before injection. After dilution with these solutions, the volume for infusion may be 100 ml or less, 75 ml or less, 50 ml or less, with an infusion time of 20 min or less, 15 minutes or less or 10 minutes or less.

The compositions of the invention may be administered either alone or in combination with other therapeutic agents having similar or different biological activities. For example, compositions of the invention may be administered in a combination therapy, i.e., either simultaneously in single or separate dosage forms or in separate dosage forms within seconds, minutes, hours, or days of each other. Examples of therapeutic agents used in such combination therapies include without limitation, chemotherapeutic agents, immunosuppressive agents, immunostimulatory, antipyretic, cytokines, opioids, cytotoxic agents, nucleolytic compounds, radioactive isotopes, receptors, pro-drug activating enzymes, which may be naturally occurring or produced by recombinant methods, anti-inflammatory or anti-rheumatic agents, antibiotics, protease inhibitors, growth factors, osteo-inductive factors, analgesics, anticonvulsants, antidepressants, natural opium alkaloids, anti-epileptics, non-selective monoamine reuptake inhibitors, anilides, diphenylpropylamine derivatives, acetic acid derivatives and related substances, platelet aggregation inhibitors excluding heparin, carboxamide derivatives, propionic acid derivatives, salicylic acid derivatives, local anesthetics, topical non-steroidal anti-inflammatory compounds, opium alkaloids and derivatives, anesthetics for topical use, drugs used in opioid dependence, hydantoin derivatives, oripavine derivatives, phenylpiperidine derivatives, proton pump inhibitors (e.g., omeprazole and/or any of its stereoisomers), and the like.

Preparation of Compositions of the Invention

The compositions of the invention can be prepared by a variety of techniques known in the art. For example, the method may comprise combining the bendamustine with the at least one cyclodextrin, at least one non-aqueous solvent, at least about 2% water v/v of the composition, and at least one antioxidant. The components of the compositions of the invention may be combined together in a single solution or prepared as separate solutions that are then combined.

Dosage Forms Containing Compositions of the Invention

Compositions of the present invention can be provided in unit presentations. Each unit presentation can contain a single dose or multiple-doses of a composition of the invention. For example, a unit containing a composition of the present invention may contain one, two, three, four, five, six, seven, eight, nine, ten, or more doses. The units may be provided in any suitable type of sealed container known to those in the art. For example, the units may be packaged and provided in vials, ampoules, syringes, sealed bottles, or sealed bags made of pharmaceutically acceptable material, such as glass or pharmaceutically acceptable plastic.

The sealed units containing the compositions of the invention may be stable for storage for extended periods prior to administration. For example, the sealed units containing the compositions of the invention may be stable at room temperature conditions (e.g., about 25° C./60% RH) for extended periods of time (e.g., ≥1 month, ≥6 months, ≥1 year, ≥18 months, ≥2 years), with minimal degradation of the bendamustine (e.g., it retains ≥90%, ≥91%, ≥92%, ≥93%, ≥94%, ≥95%, ≥96%, ≥97%, ≥98%, ≥99% of undegraded bendamustine) and with impurities less than or equal to acceptable limits (e.g., total impurities ≤6%, ≤5%, ≤4%, ≤3%, ≤2%, ≤1%, ≤0.1%), as determined by HPLC. For example, a sealed unit dose containing the compositions of the invention may contain total impurities ≤3% in the composition resulting from the degradation of bendamustine in the composition, as determined by HPLC at a wavelength of 220 nm, at about 25° C./60% relative humidity for ≥6 months; a sealed unit dose containing the compositions of the invention may contain total impurities ≤5% in the composition resulting from the degradation of bendamustine in the composition, as determined by HPLC at a wavelength of 220 nm, at about 25° C./60% relative humidity for ≥1 year; and a sealed unit dose containing the compositions of the invention may contain total impurities ≤6% in the composition resulting from the degradation of bendamustine in the composition, as determined by HPLC at a wavelength of 220 nm, at about 25° C./60% relative humidity for ≥18 months.

The sealed units containing the compositions of the invention may also be stable at refrigerated conditions (about 2-8° C.) for even longer periods of time (e.g., ≥1 year, ≥2 years, ≥3 years, ≥4 years), with minimal degradation of the bendamustine (e.g., it retains ≥90%, ≥91%, ≥92%, ≥93%, ≥94%, ≥95%, ≥96%, ≥97%, ≥98%, ≥99% of undegraded bendamustine) and with impurities less than or equal to acceptable limits (e.g., total impurities ≤6%, ≤5%, ≤4%, ≤3%, ≤2%, ≤1%, ≤0.1%), as determined by HPLC at a wavelength of 220 nm. For example, a sealed unit dose containing the compositions of the invention may contain total impurities ≤5% in the composition resulting from the degradation of bendamustine in the composition, as determined by HPLC at a wavelength of 220 nm, at about 2-8° C. for ≥2 years.

The units containing the composition of the invention may be administered to a mammal in need thereof of bendamustine treatment parenterally, such as by subcutaneous, intramuscular, or intravenous routes.

EXPERIMENTAL

Materials and Characterization:

Bendamustine was obtained from Olon, S.P.A, Italy, PEG 400 (USP/NF) from Merck. PEG 300, PEG 200, PEG 600, and PG were obtained from Sigma Aldrich (analytical or meeting USP specifications). Tocopherol, monothioglycerol, meglumine, butylated hydroxy toluene, and propylene glycol were of analytical grade and were purchased from Sigma-Aldrich. Hydroxy propyl-β-cyclodextrin, (Kleptose HPB, parenteral grade) was obtained from Roquette, Germany.

Stability of bendamustine formulations was assessed using HPLC method, which used gradient elution as mentioned below:

Mobile phase A: 90% of trifluoroacetic acid solution in water (0.1% v/v TFA) and 10% acetonitrile.
Mobile phase B: 50% of trifluoroacetic acid solution in water (0.1% v/v TFA) and 50% acetonitrile.
Flow rate: 1 mL/minute.
Detection: 220 nm
Column: Column: Symmetry C-18 (250×4.6 mm) 5 μm, or equivalent
Column temperature: 25° C.
Sample temperature: 5° C.
Injection volume: 20 μL
Gradient:

| Time (Minutes) | % Mobile phase A | % Mobile phase B |
|---|---|---|
| 0 | 100 | 0 |
| 13 | 50 | 50 |
| 17 | 30 | 70 |
| 19 | 10 | 90 |
| 24 | 10 | 90 |
| 25 | 100 | 0 |
| 29 | 100 | 0 |

The impurities were calculated using total area and area of individual areas of peaks.

Example 1: Solubility of Bendamustine in Selected Solvents

Bendamustine HCl was added in 5-10 mg increments to vials containing PG, PEG 200, PEG 300, PEG 400, and PEG 600, and the mixtures were sonicated. Sonication was stopped when the solution remained turbid after 8-10 minutes of sonication. Table 1 shows the solubility of the bendamustine in each non-aqueous solvent.

TABLE 1

| Solubility of bendamustine in non-aqueous solvents | |
|---|---|
| Solvent | Solubility of bendamustine |
| PG | >50 mg/mL |
| PEG 200 | >50 mg/mL |
| PEG 300 | >50 mg/mL |
| PEG 400 | 25-30 mg/mL |
| PEG 600 | 8-10 mg/mL |

Note: The solubility might be slightly overestimated because of the generation of heat during long sonication.

Based on its solubility, bendamustine had adequate solubility in PG, PEG 200, and PEG 300. However, its solubility was insufficient in PEG 400 and PEG 600.

Example 2: Solubility of Hydroxy Propyl-β-Cyclodextrin (HPβCD) in Non-Aqueous Solvents PG, PEG 200, PEG 300, PEG 400, and PEG 600 were added to vials containing hydroxy propyl-β-cyclodextrin (HPβCD) (50 mg) and sonicated for 10 minutes. The vials were observed for clarity of solution. Table 2 describes the appearance of the solutions for each non-aqueous solvent.

TABLE 2

Solubility of HPβCD in non-aqueous solvents

| Solvent | Amount of HPβCD per mL of solvent | Physical observation |
|---|---|---|
| PG | 50 mg | Clear |
| PEG 200 | 50 mg | Clear |
| PEG 300 | 50 mg | Clear |
| PEG 400 | 50 mg | Turbid |
| PEG 600 | 50 mg | Turbid |

The solubility of HPβCD in PG, PEG 200, and PEG 300 was adequate. HPβCD, however, was insoluble in PEG 400 and PEG 600.

Example 3: Solubility of Bendamustine in Non-Aqueous Solvents in the Presence of Cyclodextrin Bendamustine HCl was added to vials containing 50 mg of HPβCD per mL and PG, PEG 200, PEG 300, PEG 400, or PEG 600, and the mixtures were sonicated for about 8-10 minutes after each addition of bendamustine. The addition of bendamustine was stopped when the solutions remained turbid even after sonication for about 8-10 minutes. Table 3 shows the solubility of bendamustine in each non-aqueous solvent and the appearance of the resulting liquid mixtures.

TABLE 3

Solubility and appearance of bendamustine in HPβCD and non-aqueous solvents

| Solvent | Amount of HPβCD per mL of solvent | Solubility of Bendamustine | Appearance of resulting liquid mixture |
|---|---|---|---|
| PG | 50 mg | 50 mg/mL | Clear solution |
| PEG 200 | 50 mg | 50 mg/mL | Clear solution |
| PEG 300 | 50 mg | 50 mg/mL | Clear solution |
| PEG 400 | 50 mg | 40-45 mg/mL | Clear solution |
| PEG 600 | 50 mg | 25-30 mg/mL | Clear solution |

Unexpectedly, the solubility of both bendamustine and HPβCD increased drastically. The 50 mg of HPβCD was solubilized in 1 mL of PEG 400 and PEG 600 in the presence of bendamustine. Similarly, the solubility of bendamustine also increased in the presence of HPβCD; its solubility was close to double in PEG 400 and greater than three times as much in PEG 600. In most previously reported studies, cyclodextrins increased the solubility of drugs, but here the bendamustine improved the solubility of cyclodextrin. This unexpected result was very useful in formulating the insoluble and unstable bendamustine.

Example 4: Formulations of Bendamustine with Cyclodextrin Selected Solvents

Bendamustine HCl was added to vials containing monothioglycerol (MTG), HPβCD, and one of PG, PEG 200, PEG 300, PEG 400, and PEG 600 (Table 4), and their stability was determined by HPLC at 40° C./75% RH at two and three months (Table 5).

TABLE 4

Formulations of bendamustine with different non-aqueous solvents

| Ingredients | Formulation | | | | |
| | 1 | 2 | 3 | 4 | 5 |
|---|---|---|---|---|---|
| bendamustine HCl | 25 mg | 25 mg | 25 mg | 25 mg | 25 mg |
| MTG | 10 mg | 10 mg | 10 mg | 10 mg | 10 mg |
| HPβCD | 50 mg | 50 mg | 50 mg | 50 mg | 50 mg |
| PG | 1 mL | — | — | — | — |
| PEG 200 | — | 1 mL | — | — | — |
| PEG 300 | — | — | 1 mL | — | — |
| PEG 400 | — | — | — | 1 mL | — |
| PEG 600 | — | — | — | — | 1 mL |

TABLE 5

Stability data of bendamustine formulations 1-5

| Formulation | Stability at 40° C./75% RH 2 months | | Stability at 40° C./75% RH 3 months | |
| | Peak purity (%) | Total Impurity (%) | Peak purity (%) | Total Impurity (%) |
|---|---|---|---|---|
| 1 | 20.54 | 79.47 | 12.44 | 87.56 |
| 2 | 75.82 | 24.18 | 71.00 | 29.00 |
| 3 | 93.23 | 6.71 | 88.98 | 11.02 |
| 4 | 98.51 | 2.01 | 97.47 | 2.53 |
| 5 | 98.87 | 1.13 | 98.42 | 1.58 |

Note:
All the formulations were stored in screw cap vials, which are not completely moisture resistant. The impurities presented are cumulative of additional impurities generated and increase in existing impurities. In subsequent examples also, the same pattern is followed for reporting impurities.

The stability of formulation 5 with PEG 600 was good with a total impurity after 3 months of 1.58%. This was followed by formulation 4 with PEG 400 with a total impurity of 2.53%. These results indicate that the presence of cyclodextrin in a non-aqueous solvent where it is insoluble allows the cyclodextrin to interact with bendamustine and form a complex, resulting in solubilization of both host and guest. Such interactions led to the stabilization of bendamustine.

In other solvents, such as PEG 200 and PEG 300, both bendamustine and cyclodextrin are soluble to a greater extent. It is expected that, when a drug and cyclodextrin are put into a solvent in which both are soluble, host-guest interaction would be minimal and the drug would possibly exist as a free entity, as the environment would not force a complexation or interaction.

On the other hand, the literature reports that cyclodextrins improve solubility and stability of drugs in water. However, no such observations were reported for organic solvents where cyclodextrin is insoluble.

Interestingly, the stability of bendamustine had an inverse relationship with the solubility of bendamustine in solvent. Therefore, in a solvent in which the bendamustine is slightly soluble, the bendamustine must complex with cyclodextrin thereby increasing solubility and stability. Another unusual observation was that the solubility of cyclodextrin also improved. In all the formulations, only one impurity is major, presumably the PEG ester at RRT of around 1.05 followed by other esters.

Example 5: Repetition of Formulation 5 with PEG 400 for Stability Testing

Bendamustine HCl, MTG, HPβCD, and PEG 400 were again mixed in a vile as formulation 6 (Table 6), and its stability was determined by HPLC at 40° C./75% RH at one, two, and three months, and at 25° C./60% RH at 3 months and 4 months, 20 days (Table 7).

TABLE 6

Formulation 6 with PEG 400

| Ingredients | Formulation 6 |
|---|---|
| bendamustine HCl | 25 mg |
| HPβCD | 50 mg |
| MTG | 10 mg |
| PEG 400 | 1 ml |

TABLE 7

Stability data of Formulation 6

| Trial | 40° C./75% RH (% Total impurity) | | | 25° C./60% RH (% Total impurity) | |
|---|---|---|---|---|---|
| | 1 month | 2 months | 3 months | 3 months | 4 months, 20 days |
| Trial-2 | 1.68 | 1.72 | 2.21 | Not measured. | Not measured. |
| Trial-3 | 1.5 | 1.8 | 4.01 | stable, no additional impurities | stable, no additional impurities |
| Trial-4 | 0.35 | 2.01 | 2.5 | Not measured. | Not measured. |

When stored in glass screw cap vials of different design, which were not completely moisture resistant, the stability of formulation 6 was inconsistent, as moisture entry into the vials was not regulated and inconsistent. The moisture entry into the vials was confirmed by storing a hygroscopic powder in the glass vials. Formulation 6 was more stable at 25° C./60% RH and there was no correlation between 25° C./60% RH and 40° C./75% RH. This could be due to moisture being more of a culprit than temperature, and the moisture uptake into the vials was greater at 40° C./75% RH.

Example 6: Formulations with Meglumine as Alkalizer in PEG 400

Bendamustine HCl was added to vials containing HPβCD, MTG, PEG 400, and meglumine (as an alkalizer) (Table 8), and their stability was determined by HPLC at 40° C./75% RH at one, two, and three months, and at 25° C./60% RH at 3 months (Table 9).

TABLE 8

Formulations with meglumine

| Ingredients | Formulation | |
|---|---|---|
| | 7 | 8 |
| bendamustine HCl | 25 mg | 25 mg |
| HPβCD | 50 mg | 50 mg |
| MTG | 10 mg | 5 mg |
| PEG 400 | 1 ml | 1 ml |
| meglumine | 0.5 mg | 0.6 mg |

TABLE 9

Stability data of formulations with meglumine

| Formulation | 40° C./75% RH (% Total impurity) | | | 25° C./60% RH (% Total impurity) |
|---|---|---|---|---|
| | 1 month | 2 months | 3 months | 3 months |
| 7 | 0.2% | 1.66 | 1.99 | 0.45 |
| 8 | below detection limit | 0.8-0.9 | 3.72 | not done |

The stability of the formulations with meglumine was moderately improved with the inclusion of meglumine. However, the stability depended on the moisture uptake into the container and impurity levels varied between formulations.

Example 7: Formulations with Combinations of PEG 400 and PEG 600

Bendamustine HCl was added to vials containing HPβCD, MTG, PEG 400, PEG 600, and, in some vials, NaOH (Table 10), and their stability in screw cap vials, sealed in aluminum pouches, was determined by HPLC at 40° C./75% RH at one, two, and three months, and at 25° C./60% RH at 3 months (Table 11).

TABLE 10

Formulations 9-12

| Ingredients | Formulation | | | |
|---|---|---|---|---|
| | 9 | 10 | 11 | 12 |
| bendamustine HCl | 25 mg | 25 mg | 25 mg | 25 mg |
| HPβCD | 50 mg | 50 mg | 50 mg | 50 mg |
| MTG | 10 mg | 10 mg | 10 mg | 10 mg |
| PEG 400 | 0.875 mL | 0.80 mL | 0.875 mL | 0.80 mL |
| PEG 600 | 0.125 mL | 0.20 mL | 0.125 mL | 0.20 mL |
| NaOH | 0.4 mg | 0.4 mg | — | — |

TABLE 11

Stability data of formulations 9-12 (screw cap vials, sealed in aluminum pouches)

| Formu-lation | 40° C./75% RH (% total impurity) | | | 25° C./60%RH (% total impurity) |
|---|---|---|---|---|
| | 1 Month | 2 months | 3 months | 3 months |
| 9 | below detection limit | 0.64 | 1.13 | stable, no new impurity, no increase in total impurities |
| 10 | below detection limit | 0.36 | 0.70 | stable, no new impurity, no increase in total impurities |
| 11 | 0.18 | 1.22 | 4.96 | stable, no new impurity, no increase in total impurities |
| 12 | below detection limit | 1.32 | 6.05 | stable, no new impurity, no increase in total impurities |

Note:
The assay of all the formulations dropped by 15-20% at the end of three months at 40° C./75% RH. The assay remained unaffected at 25° C./60% RH.

Based on the stability data, purity was maintained for formulations 9-10 when they were stored in a moisture resistant package (screw cap vials in sealed aluminum pouches). Indeed, their total impurities were <1.5%. Degradation of formulations 11 and 12 increased rapidly after 2 months. A moderate amount of alkali is needed for stabilization. At accelerated conditions, the assay dropped by about 15-20% at the end of three months. Although impurities were controlled in formulations 9-10, the assay needed to be maintained.

Example 8: Formulations with Tocopherol

Bendamustine HCl was added to vials containing tocopherol, HPβCD, NaOH, and PEG 400 (Table 12), and their stability was determined by HPLC at 40° C./75% RH at two months, 23 days (Table 13).

TABLE 12

Formulations 13-16

| Ingredients | Formulation | | | |
|---|---|---|---|---|
| | 13 | 14 | 15 | 16 |
| bendamustine HCl | 25 mg | 25 mg | 25 mg | 25 mg |
| α-tocopherol | 0.8 mg | 0.9 mg | 1.0 mg | 1.2 mg |
| HPβCD | 50 mg | 50 mg | 51 mg | 51 mg |
| NaOH | 0.4 mg | 0.4 mg | 0.4 mg | 0.4 mg |
| PEG 400 | 1 mL | 1 mL | 1 mL | 1 mL |

TABLE 13

Stability data of formulations 13-16

| | 40° C./75% RH, 2 months 23 days | |
|---|---|---|
| Formu-lation | Assay | % Impurity (additional than standard API) |
| 13 | 97 to 104% of initial value | <0.3% |
| 14 | | <0.3% |
| 15 | | <0.3% |
| 16 | | <0.3% |

Bendamustine HCl was also added to vials containing HPβCD, MTG, PEG 400, NaOH, and α-tocopherol (Table 14), and their stability was determined by HPLC at 40° C./75% RH at three months, 11 days (Table 15).

TABLE 14

Formulations 17-18

| Ingredients | Formulation | |
|---|---|---|
| | 17 | 18 |
| bendamustine HCl | 25.0 mg | 25.0 mg |
| HPβCD | 50.0 mg | 50.0 mg |
| MTG | 5.0 mg | 5.0 mg |
| PEG 400 | 1.0 ml | 1.0 ml |
| NaOH | 0.4 mg | 0.4 mg |
| α-tocopherol | 0.6 mg | 0.8 mg |

TABLE 15

Stability data of formulations 17-18

| | 40° C./75% RH, 3 months 11 days | |
|---|---|---|
| Formu-lation | Assay | % Impurity (additional than standard API) |
| 17 | 97 to 102% of initial value | <0.5% |
| 18 | | <0.5% |

Inclusion of tocopherol improved stability of bendamustine and its assay was maintained close to the initial value. Both assay and impurities were well controlled for formulations with these excipients. The presence of very low amounts of tocopherol improved stability significantly, both in terms of assay and impurities. The mechanism of this drastic, and unexpected, stabilization effect by tocopherol is not understood. Also, after dilution with water, tocopherol did not phase separate or precipitate due to the presence of the cyclodextrin solubilizer. In the absence of bendamustine, tocopherol solution in PEG 400 containing cyclodextrin when diluted with water turned milky white due to precipitation of tocopherol. This result clearly indicates that physical interaction between bendamustine, cyclodextrin, and tocopherol is responsible for the observed stability and solubility upon dilution with water.

Example 9: Semi-Aqueous Formulations of Bendamustine

Bendamustine HCl was also added to vials containing HPβCD, MTG, butylated hydroxy toluene (BHT), tocopherol, NaOH, water (10% v/v), and PEG 400 (Table 16), and their stability was determined by HPLC at 40° C./75% RH at three months (Table 17) and at 25° C./60% RH at three months and six months (Table 18) and 13 months (Table 19).

TABLE 16

Compositions of bendamustine containing water (10% v/v) and PEG 400

| Ingredients | Formulation | | | |
|---|---|---|---|---|
| | 19 | 20 | 21 | 22 |
| bendamustine HCl | 25 mg | 25 mg | 25 mg | 25 mg |
| HPβCD | 25 mg | 50 mg | 25 mg | 50 mg |
| MTG | 5 mg | 5 mg | — | — |
| Butylated Hydroxy Toluene (BHT) | — | — | 1 mg | 1 mg |
| α-tocopherol | 1.2 mg | 1.2 mg | 1.2 mg | 1.2 mg |
| NaOH | 0.4 mg | 0.4 mg | 0.4 mg | 0.4 mg |
| Water | 0.1 ml | 0.1 ml | 0.1 ml | 0.1 ml |
| PEG 400 | 0.9 ml | 0.9 ml | 0.9 ml | 0.9 ml |

TABLE 17

Stability data of compositions of bendamustine containing water (10% v/v) and PEG 400 at 3 months at 40° C./75% RH

| Parameters | 3 months at 40° C./75% RH | | | |
|---|---|---|---|---|
| | 19 | 20 | 21 | 22 |
| % Purity | 95.83 | 95.95 | 96.39 | 95.91 |
| % Area (Ester Impurity) | 2.17 | 2.05 | 1.81 | 2.09 |
| % Area (HP1 Impurity) | 2.00 | 2.00 | 1.86 | 2.00 |

TABLE 18

Stability data at 25° C./60% RH, 3 months and 6 months

| Parameters | 19 | 20 | 21 | 22 |
|---|---|---|---|---|
| 3 months at 25° C./60% RH | | | | |
| Bendamustine Peak purity (Area % of Bendamustine peak) | 99.76 | 99.73 | 99.57 | 99.57 |
| Total Impurity (% Area) (Additional against standard injection) | 0.24 | 0.27 | 0.43 | 0.43 |
| Assay remained between 97-100% for all formulations | | | | |
| 6 months at 25° C./60% RH | | | | |
| Bendamustine Peak purity (Area % of Bendamustine peak) | 99.17 | 99.04 | 99.10 | 98.90 |
| Total Impurity (% Area) (Additional against standard injection) | 0.83 | 0.96 | 0.89 | 1.1 |
| Assay remained between 97-100% for all formulations | | | | |

TABLE 19

Stability data at 25° C./60% RH, 13 months

| | 19 | | | 20 | | | 21 | | | 22 | | |
|---|---|---|---|---|---|---|---|---|---|---|---|---|
| | Assay | Impurity (%) | Retention time | Assay | Impurity (%) | Retention time | Assay | Impurity (%) | Retention time | Assay | Impurity (%) | Retention time |
| Condition | (%) | 15.33 | 16.00 | (%) | 15.33 | 16.00 | (%) | 15.33 | 16.00 | (%) | 15.33 | 16.00 |
| 25° C./60% RH 13 months | 90.07 | 0.22 | 1.20 | 90.65 | 0.135 | 1.06 | 90.89 | 0.246 | 1.18 | 91.00 | 0.44 | 1.12 |

The results of the stability studies of formulations 19-22 indicate that even formulations containing a portion of water are stable due to the presence of both cyclodextrin and tocopherol. The stability of bendamustine is reported to be very poor with the formation of hydrated impurities in a short period of time. Surprisingly, as demonstrated by these stability studies, formulations 19-22 can have a shelf life of >2 years if they are stored in refrigerated conditions. Unexpectedly, formulations 19-22 were found to be stable at 25° C./60% RH, 13 months. However, the accelerated stability data (40° C./75% RH) did not correlate to the real time testing (25° C./60% RH)—the 40° C./75% RH data indicates instability of the formulations at room temperature but were found to be stable at 25° C./60% RH for more than a year.

Example 10: Formulations of Bendamustine with Water (20% v/v)

Bendamustine HCl was added to vials containing HPβCD, MTG or butylated hydroxy toluene, tocopherol, NaOH, PEG 400 and water (20% v/v) (Table 20), and their stability was determined by HPLC at 40° C./75% RH at six months (Table 21), 25° C./60% RH at six months (Table 22), and at refrigerated conditions (2-8° C.) (Table 23).

TABLE 20

Bendamustine formulations with water (20% v/v)

| Ingredients | 23 | 24 | 25 | 26 | 27 |
|---|---|---|---|---|---|
| Bendamustine HCl | 25 mg | 25 mg | 25 mg | 25 mg | 25 mg |
| HPβCD | 60 mg | 60 mg | 60 mg | 60 mg | 60 mg |
| Monothioglycerol | 5 mg | 5 mg | — | — | — |
| α-Tocopherol | 1.0 mg | 1.2 mg | 1.0 mg | 1.2 mg | 1.0 mg |
| Butylated Hydroxy Toluene | — | — | 1.0 mg | 1.0 mg | — |
| NaOH | 0.4 mg | 0.4 mg | 0.4 mg | 0.4 mg | 0.4 mg |
| Water | 0.2 ml | 0.2 ml | 0.2 ml | 0.2 ml | 0.2 ml |
| PEG 400 | 0.8 ml | 0.8 ml | 0.8 ml | 0.8 ml | 0.8 ml |

TABLE 21

Stability data of formulations 23-27 at 40° C./75% RH 6 months

| Formulations | 40° C./75% RH 6 months % Total Impurity |
|---|---|
| 23 | 28.94 |
| 24 | 29.17 |
| 25 | 27.75 |

TABLE 21-continued

Stability data of formulations 23-27 at 40° C./75% RH 6 months

| Formulations | 40° C./75% RH 6 months % Total Impurity |
|---|---|
| 26 | 28.28 |
| 27 | 28.2 |

TABLE 22

Stability data of formulations 23-27 at 25° C./60% RH, 6 months

| | Formulation | | | | | | | | | |
|---|---|---|---|---|---|---|---|---|---|---|
| | 23 | | 24 | | 25 | | 26 | | 27 | |
| Conditions | Assay (%) | Impurity (%) | Assay (%) | Impurity (%) | Assay (%) | Impurity (%) | Assay (%) | Impurity (%) | Assay (%) | Impurity (%) |
| 25° C./60% RH 6 months | 95.58 | 2.5 | 94.59 | 2.58 | 96.05 | 2.71 | 94.68 | 3.47 | 95.33 | 3.42 |

TABLE 23

Stability data of formulations 23-27 at refrigerated conditions (2-8° C.), 1 year

| | Formulation | | | | | | | | | |
|---|---|---|---|---|---|---|---|---|---|---|
| | 23 | | 24 | | 25 | | 26 | | 27 | |
| Conditions | Assay (%) | Impurity (%) | Assay (%) | Impurity (%) | Assay (%) | Impurity (%) | Assay (%) | Impurity (%) | Assay (%) | Impurity (%) |
| Refrigerated conditions (2-8° C.), 1 year | 104.05 | 0.653 | 102.73 | 0.559 | 105.31 | 0.744 | 102.7 | 0.615 | 105.1 | 0.664 |

Even though formulations 23-27 contained water (20% v/v), they remained stable at refrigerated conditions for more than year. The formulations were found to be unstable at 40° C./75% RH with >28% impurities, but demonstrated moderate stability at 25° C./60% RH with up to 3% additional impurities. Predictions of instability by the data at 25° C./60% RH did not apply to the formulations at refrigerated conditions.

Results and Discussion

Bendamustine was slightly soluble in PEG's of higher molecular weight (e.g., PEG 400 and PEG 600), but the solubility was not enough to achieve the required solubilization for accommodating a dose of bendamustine in a given volume of solvent.

Cyclodextrin (e.g., HPβCD) increased the solubility of bendamustine in non-aqueous solvents where it is slightly soluble, and also cyclodextrin itself is not soluble (e.g., PEG 400 and PEG 600).

The formation of a complex or physical interaction between bendamustine and cyclodextrin increased the solubility of both molecules. As a result of such interaction, the stability of bendamustine increased.

Such stability improvement was not observed with lower molecular weight PEG's (e.g., PEG 200 and PEG 300) and PG, where both bendamustine and cyclodextrin are soluble.

Surprisingly, the addition of significant amounts of water (e.g., up to 20 wt %) did not significantly alter the stability of the formulations. Formulations 23-27 possessed substantial stability of bendamustine even in the presence of water and PEG 400. The cyclodextrin based solubilization of bendamustine in solvents such as PEG 400 has a positive effect on stability, but, contrary to expectations, the inclusion of certain amounts of water provide a synergistic effect on stability. The inclusion of cyclodextrin in aqueous solutions of bendamustine improved the stability of bendamustine. In sum, the stabilization effect of cyclodextrin on bendamustine is enhanced if the solvent system is semi-aqueous, rather than solely or substantially aqueous or non-aqueous.

What is claimed is:

1. A stable liquid pharmaceutical composition comprising:
    a) about 0.1 wt % to about 50 wt % of bendamustine HCl;
    b) about 0.1 wt % to about 40 wt % of hydroxy propyl-β-cyclodextrin;
    c) about 40% to about 98% of PEG 400;
    d) at least about 2% water v/v of the composition; and
    e) about 0.01 to about 10 wt % of a mixture of monothioglycerol and tocopherols,
    wherein the composition contains total impurities ≤6% in the composition resulting from the degradation of bendamustine in the composition, as determined by HPLC at a wavelength of 220 nm, at about 25° C/60% relative humidity for ≥18 months.

2. The composition of claim 1, wherein the composition contains <0.1 wt % of organic small molecule alcohols.

3. The composition of claim 1, wherein the composition contains no organic small molecule alcohol.

4. The composition of claim 1, wherein the PEG 400 is present in an amount ranging from about 70% to about 90% v/v of the composition and the water is present in an amount ranging from about 10% to about 30% v/v of the composition.

5. The composition of claim 4, wherein the composition contains no propylene glycol.

6. The composition of claim 1, comprising at least one further pharmaceutically acceptable excipient.

7. The composition of claim 1, comprising at least one further solubilizer.

8. The composition of claim 1, wherein the composition contains total impurities ≤5% in the composition resulting from the degradation of bendamustine in the composition, as determined by HPLC at a wavelength of 220 nm, at about 2-8° C. for ≥2 years.

9. A stable liquid pharmaceutical composition comprising:
   a) about 0.1 wt % to about 50 wt % of bendamustine HCl;
   b) about 0.1 wt % to about 40 wt % of hydroxy propyl-β-cyclodextrin;
   c) about 40% to about 98% of PEG 400;
   d) at least about 2% water v/v of the composition; and
   e) about 0.01 to about 10 wt % of a mixture of monothioglycerol and tocopherols,
   wherein the composition contains total impurities ≤5% in the composition resulting from the degradation of bendamustine in the composition, as determined by HPLC at a wavelength of 220 nm, at about 2-8° C. for ≥2 years.

10. The composition of claim 9, wherein the composition contains <0.1 wt % of organic small molecule alcohols.

11. The composition of claim 9, wherein the composition contains no organic small molecule alcohol.

12. The composition of claim 9, wherein PEG 400 is present in an amount ranging from about 70% to about 90% v/v of the composition and the water is present in an amount ranging from about 10% to about 30% v/v of the composition.

13. The composition of claim 12, wherein the composition contains no propylene glycol.

14. The composition of claim 9, comprising at least one further pharmaceutically acceptable excipient.

15. The composition of claim 9, comprising at least one further solubilizer.

16. A method of treating cancer comprising the administration of an effective amount of a composition of claim 1 to a mammal in need thereof, wherein the cancer is selected from the group consisting of chronic lymphocytic leukemia, multiple myeloma, indolent B-cell non-Hodgkin's lymphoma, and mixtures thereof.

17. The method of claim 16, wherein the composition is not diluted before administering to the mammal.

18. A method of treating cancer comprising the administration of an effective amount of a composition of claim 9 to a mammal in need thereof, wherein the cancer is selected from the group consisting of chronic lymphocytic leukemia, multiple myeloma, indolent B-cell non-Hodgkin's lymphoma, and mixtures thereof.

19. The method of claim 18, wherein the composition is not diluted before administering to the mammal.

* * * * *